CHRYSANTHEMUM PLANT
Filed April 24, 1973 2 Sheets-Sheet 1
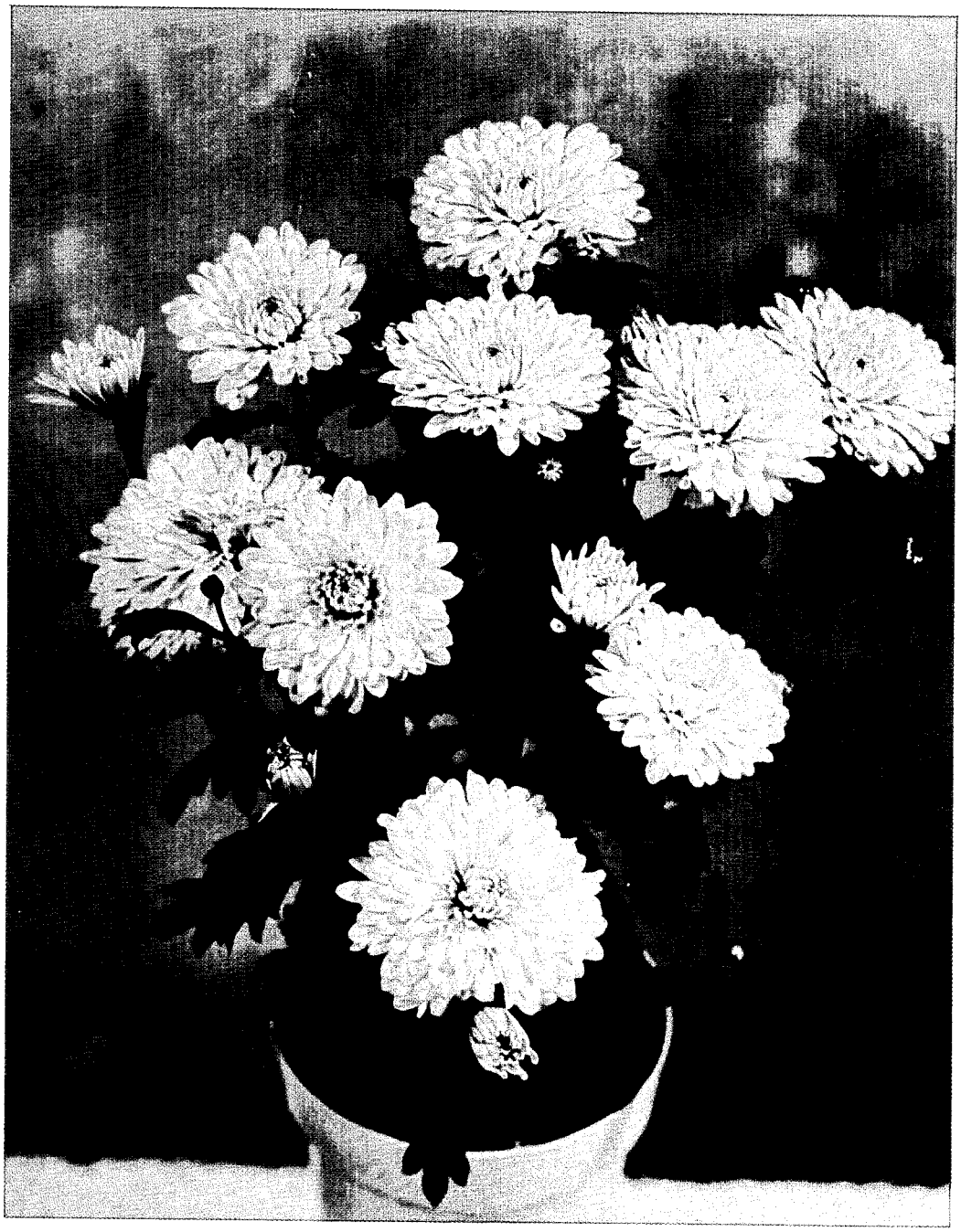

CHRYSANTHEMUM PLANT
Filed April 24, 1973 2 Sheets-Sheet 2
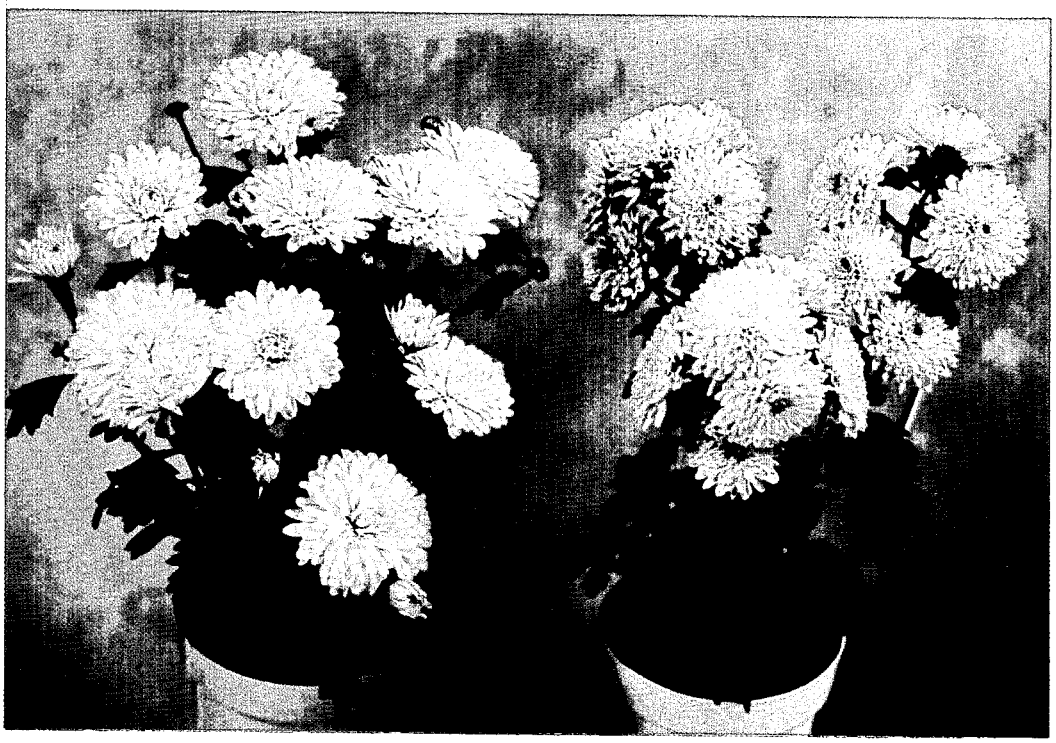

United States Patent Office

Plant Pat. 3,552

Patented May 21, 1974

3,552

CHRYSANTHEMUM PLANT

Walter H. Jessel, Jr., Doylestown, and William E. Duffett, Akron, Ohio, assignors to Yoder Brothers, Inc., Barberton, Ohio

Filed Apr. 24, 1972, Ser. No. 247,192

Int. Cl. A01h *5/00*

U.S. Cl. Plt.—75 1 Claim

The present invention comprises a new and distinct cultivar of chrysanthemum plant which is a seedling of #6055-1 × #105/61B. Both parents are unpatented and are identified for breeding purposes by the above numbers.

The new cultivar can be compared in certain respects to Grandchild, an unpatented but popular pink garden chrysanthemum well known in the trade. The new cultivar is likewise in the garden chrysanthemum category, and has a similar decorative flower form.

The new cultivar is distinguished from Grandchild by the following characteristics, when grown under comparable conditions.

1. Flowers approximately one-half inch larger in diameter.
2. Four to six days longer keeping quality.
3. A lighter, smoother, pastel pink color with less lavender tones.
4. The flower fades to a smoother, more uniform, overall color as it ages.
5. Flowering plants are approximately one inch shorter in height, approximately eight inches greater in diameter, and average three more breaks per plant when flowered naturally as field grown plants from plantings made in mid-June and given a single pinch.

6. Larger, darker green foliage which is more deeply indented and serrated.
7. Two to five days later response in natural season outdoor flowerings planted in mid-June and given a single pinch.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 8 weeks, and the following detailed description is based on observations made of the new cultivar at or in a greenhouse in Barberton, Ohio. The response time, blooming period, color, and total vigor may vary significantly with varying environmental conditions such as temperature, day length, and light intensity. Suggested flowering in the northern and western United States is from April through October, and Florida, January through February.

The accompanying drawings show the unique characteristics of the new cultivar, the color being as nearly true as possible with color illustrations of this type. Sheet 1 comprises the new cultivar shown in a pot, and sheet 2 comprises a comparison photograph, with the new cultivar appearing on the left and Grandchild on the right.

In the description which follows, color references are made to the Munsell Color Book, 1963 edition, and comparisons are made with the cultivar Grandchild. Where only a single value or designation appears for the new cultivar, it applies also to the comparison cultivar Grandchild.

Botanical classification: *Chrysanthemum morifolium*

| | Elegant Cushion | Grandchild |
|---|---|---|
| Bloom: | | |
| Size | 2" | 1½". |
| Fully expanded | 2½" | 2". |
| Borne | Clusters on elongated pedicels | |
| Stems | Strong | |
| Form | Decorative | |
| Permanence | 14 to 16 days | 10 days. |
| Color: | | |
| Center of flower | Light pink, 2.5RP9/2 | Dark pink, 10P6/6. |
| Base of petals | Pink, 5RP8/4 | Light pink, 10P9/1. |
| Inside of petals | Pink, 5RP8/4 to light pink, 2.5RP9/2 | Dark pink, 10P6/6 to light pink, 10P9/2. |
| Reverse of petals | Light pink, 2.5RP9/2 | Dark pink, 10P8/4 to light pink, 10P9/2. |
| Tonality from a distance | Light pink | Light pink with dark pink center. |
| Discoloration | Light pink, 2.5RP9/2 | Light pink, 10P9/2. |
| Petals: | | |
| Texture | Smooth | |
| Appearance and form | Tubular at base, flaring ¼ way to a flat keel, tapering to a blunt point. | Open at base, broad shallow keel, tapering to a blunt point. |
| Arrangement | Composite, whorled on a single receptacle | |
| Persistence | Resist shatter | |
| Fragrance | Typical chrysanthemum | |
| Reproductive organs: | | |
| Stamen, anthers | 0-20 | |
| Pollen | None to scant | |
| Arrangement | Clustered in center of flower, if present | |
| Styles | Present both ray and disc florets | |
| Length | Short | |
| Overies | At the base of petal attached to receptacle | |
| Plant: | | |
| Form | Herbaceous | |
| Growth | Compact-spreading | |
| Height | Approximately 14" when grown as a natural flowering field grown crop in mid-June and given a single pinch. | Approximately 15" when grown as a natural flowering field grown crop in mid-June and given a single pinch. |
| Spread | Approximately 28" when grown as a natural flowering field grown crop in mid-June and given a single pinch. | Approximately 20" when grown as a natural flowering field grown crop in mid-June and given a single pinch. |
| Foliage: | | |
| Top side | Very dark green, 7.5GY2/4 | Dark green, 10GY2/4. |
| Size | 4½" long, 2¼" wide | 3" long, 2" wide. |
| Quantity | Numerous | |
| Shape | Spatulate lobed | |
| Texture | Smooth | |
| Ribs and veins | Prominent | |
| Edge | Indented | Moderately indented. |
| Serration | Moderate | Very slight. |
| Under side | Green, 7.5GY4/4 | Light green, 7.5GY5/4. |
| Stipules | Rudimentary | |

We claim:

1. A new and distinct cultivar of chrysanthemum characterized particularly as to its uniqueness when compared to the garden chrysanthemum cultivar Grandchild by its flowers which are approximately one-half inch larger in diameter; four to six days longer keeping quality; a lighter, smoother, pastel pink color with less lavender tones, which fades to a smoother, more uniform, overall color as the flower ages; its approximately one inch shorter height, approximately eight inches greater diameter, and approximately three more breaks per plant when flowered naturally as field grown plants from plantings made in mid-June and given a single pinch, by its larger, darker green foliage which is more deeply indented and serrated, and by its two to five days later response in natural season outdoor flowerings planted in mid-June and given a single pinch.

No references cited.

ROBERT E. BAGWILL, Primary Examiner